(12) United States Patent
Yarbrough et al.

(10) Patent No.: US 7,399,891 B2
(45) Date of Patent: Jul. 15, 2008

(54) PROCESS FOR ALCOHOL PRODUCTION BY SELECTIVE ETHER DECOMPOSITION

(75) Inventors: Charles M Yarbrough, Baton Rouge, LA (US); Brian William Roberts, Baton Rouge, LA (US); Dennis Jay Davoren, Baton Rouge, LA (US); Kenneth Joseph Buturla, Baton Rouge, LA (US); Carl Stotz Katzenstein, Baton Rouge, LA (US); Doron Levin, Annandale, NJ (US); Hans Georg Korsten, Fairfax, VA (US); Vijay Swarup, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 415 days.

(21) Appl. No.: 11/147,919

(22) Filed: Jun. 8, 2005

(65) Prior Publication Data
US 2006/0281954 A1  Dec. 14, 2006

(51) Int. Cl.
*C07C 33/02* (2006.01)

(52) U.S. Cl. .............. 568/908; 568/899; 568/866; 568/867; 585/640; 585/855

(58) Field of Classification Search ........... 568/908, 568/899, 866, 867; 585/640, 855
See application file for complete search history.

(56) References Cited

U.S. PATENT DOCUMENTS

| | | | |
|---|---|---|---|
| 2,519,061 A | 8/1950 | Mason | |
| 2,529,061 A | 11/1950 | Vergnaud et al. | 195/43 |
| 4,254,290 A | 3/1981 | Chambers et al. | 568/866 |
| 4,320,232 A | 3/1982 | Volkamer et al. | 568/697 |
| 4,352,945 A | 10/1982 | Bezman | 568/899 |
| 4,357,147 A | 11/1982 | Bezman | 44/56 |
| 4,398,051 A | 8/1983 | Araki et al. | 585/640 |
| 4,405,822 A | 9/1983 | Bezman | |
| 4,405,882 A | 9/1983 | Reinsch | 315/118 |
| 4,521,638 A | 6/1985 | Kida et al. | 585/640 |
| 4,581,475 A | 4/1986 | Neier et al. | 568/907 |
| 4,691,073 A | 9/1987 | Michaelson | 585/639 |
| 5,171,920 A | 12/1992 | Chaumette et al. | 585/640 |
| 5,177,301 A | 1/1993 | Knifton | 585/855 |
| 5,254,785 A | 10/1993 | Rosenfeld et al. | 585/640 |
| 5,607,892 A | 3/1997 | Chopin et al. | 502/304 |
| 6,124,232 A | 9/2000 | Chang et al. | 502/308 |
| 6,150,299 A | 11/2000 | Umemoto et al. | 502/304 |
| 6,162,757 A | 12/2000 | Chang et al. | 502/302 |
| 6,297,406 B1 | 10/2001 | Levin et al. | 568/798 |
| 7,102,037 B2 * | 9/2006 | Levin et al. | 568/908 |

FOREIGN PATENT DOCUMENTS

| | | |
|---|---|---|
| JP | A-59010528 | 1/1984 |
| JP | 62-10028 | 1/1987 |
| JP | 3-123738 | 5/1991 |
| JP | 2749664 | 5/1991 |
| JP | A-06072904 | 3/1994 |
| WO | WO96/13328 | 5/1996 |
| WO | WO 03/037506 | 5/2003 |
| WO | WO2005/066101 | 7/2005 |

OTHER PUBLICATIONS

"Production D'Isobutene de Haute Pureté par Décomposition du MTBE" by P.B. Meunier et al. in Revue de L'Institut Francais du Petrole, vol. 46, No. 3, May 1991, pp. 361 to 387.

* cited by examiner

*Primary Examiner*—Elvis O. Price
(74) *Attorney, Agent, or Firm*—Andrew B. Griffis

(57) ABSTRACT

This invention relates to a process for the production of an alcohol, the process comprising (a) reacting an olefin and water in the presence of a catalyst under conditions sufficient to form a crude alcohol stream comprising alcohol, and a dialkyl ether; (b) separating at least a portion of the crude alcohol stream into an alcohol-containing stream and a dialkyl ether stream; (c) contacting at least a portion of the dialkyl ether stream with an ether decomposition catalyst, the ether decomposition catalyst comprising a mixed metal oxide having the following composition $X_m Y_n Z_p O_q$ where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising alcohol and olefin; (d) recovering at least a portion of the olefin from the crude dialkyl ether decomposition stream; and (e) recycling at least a portion of the olefin recovered in step (d) to step (a).

25 Claims, 5 Drawing Sheets

PROCESS FOR ALCOHOL PRODUCTION BY SELECTIVE ETHER DECOMPOSITION

FIELD OF THE INVENTION

This invention relates to an integrated process for the production of alcohols. More specifically this invention relates to an integrated process for the production of alcohols from olefins by hydration and the selective decomposition of ethers to the alcohol and olefin.

BACKGROUND OF THE INVENTION

The conversion of ethers to the corresponding alkenes and alcohols, preferably alkanols, i.e., aliphatic alcohols, is an important reaction in a number of commercial processes. Thus, for example, this reaction is used to remove ethers, such as isopropyl ether, produced as the by-products of olefin hydration processes, such as the hydration of propylene to produce isopropanol.

Various catalysts have been proposed for the decomposition of ethers, for instance, in U.S. Pat. Nos. 4,691,073; 4,254,290; 4,320,232; 4,521,638; 4,398,051; 4,357,147. "Production D'Isobutene de Haute Pureté par Décomposition du MTBE" by P. B. Meunier et al. in Revue de L'Institut Francais du Petrole, vol. 46, No. 3, May 1991, pages 361 to 387, U.S. Pat. Nos. 5,254,785, 5,177,301, 5,117,920 and Japanese Published Patent Application No. JP-A-06072904.

U.S. Pat. No. 4,352,945 describes discloses a process for producing isopropanol comprising (a) contacting water and a feedstock comprising propylene with a catalyst comprising an acid ion exchange resin in a first reaction zone under hydration conditions to produce a first stream; (b) dividing the first stream into a second stream comprising water and isopropanol and a third stream comprising diisopropyl ether; (c) contacting the third stream with a reversion catalyst in a second reaction zone under reversion conditions to produce a fourth stream; (d) separating propylene from the fourth stream; (e) recycling the propylene to step (a); and (f) recovering isopropanol from the second stream. The reversion reaction uses a silica alumina cogel catalyst.

U.S. Pat. No. 4,357,147 describes a process for producing an oxygenated fuel blending composition comprising (a) contacting water and a feedstock comprising propylene with a catalyst comprising an acid ion exchange resin in a first reaction zone under hydration conditions to produce a first stream; (b) dividing the first stream into a second stream comprising water and isopropanol and a third stream comprising diisopropyl ether; (c) contacting the third stream with a reversion catalyst in a second reaction zone under reversion conditions to produce a fourth stream; (d) separating propylene from the fourth stream; (e) oligomerizing the propylene; and (f) recovering isopropanol from the second stream and blending it with a gasoline blending hydrocarbon stream. The reversion reaction uses a silica alumina cogel catalyst.

Strategies to minimize the production of isopropyl ether (IPE) in processes for the manufacture of isopropanol include 1) running a low propylene conversion process, 2) recycling the IPE back to the reaction zone, 3) decomposing the IPE to propylene using acid catalyst, or 4) hydrolyzing the IPE to isopropyl alcohol (IPA).

However, low conversion processes create large recycle streams requiring large reactors, large amounts of catalyst, and fractionation of reactor effluent to create a highly concentrated propane stream for purging. If dilute propylene is used then a purification step is required for the propylene return stream.

Recycling the IPE back to the hydration unit is feasible because the reaction of IPE to IPA and/or propylene can be equilibrium controlled and is reversible in the hydration zone. Recycling IPE permits recovery of IPA and/or propylene from the IPE, but it does not eliminate the formation of IPE. In some cases it is not possible to recycle all of the IPE back into the feed and therefore other dispositions for the IPE must be found. Additionally, recycling IPE to the front end decreases the capacity of the unit by the amount of IPE recycled.

Thermal decomposition of ethers typically occurs at elevated temperature (typically >350° C.) and generates significant thermal side reactions that create impurities that must be removed before recycling. The recycled impurities quickly build up to unmanageable levels if the propylene is not purified.

The hydrolysis of IPE to produce IPA typically occurs at higher pressure, in the presence of an acidic catalyst, and requires significant amounts of water in the feed, which results in a need for large equipment and large water removal capability. The hydrolysis step can become hydraulically limiting if the water/IPA stream is returned to an existing unit.

Unpublished International Application No. PCT/US2004/041546 discloses a process for selectively converting a dialkyl ether to the corresponding alkene and alkanol, the process comprising contacting a feed containing at least one dialkyl ether with a catalyst comprising an acidic mixed metal oxide having the following composition:

$$X_m Y_n Z_p O_q$$

where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p and q are the atomic ratios of their respective components and, when m is 1, n is from 0.01 to 0.75, p is from 0 to 0.1, and q is the number of oxygen atoms necessary to satisfy the valence of the other components. The mixed oxides preferably contain sulfur, typically present in an amount of up to 5 wt %, such as up to 1 wt %, of the final mixed oxide composition. The mixed oxides can prepared by impregnation or by co-precipitation from a liquid mixture containing a source of Group 4 metal ions and a source of Group 3 and/or Group 6 metal ions. These catalysts exhibit both high selectivity and long catalyst lifetime when used as ether decomposition catalysts.

The ether decomposition process integrated into a commercial alcohol process, for example IPA, of the present invention enables high selectivity in the conversion of propylene to IPA and provides high purity propylene in the recycle stream.

SUMMARY OF THE INVENTION

In one aspect, the present invention resides in a process for selectively converting a dialkyl ether to the corresponding alkene and alkanol comprising contacting a feed containing at least one dialkyl ether with a catalyst comprising an acidic mixed metal oxide having the following composition:

$$X_m Y_n Z_p O_q$$

where X is at least one metal selected from Group 4 of the Periodic Table of Elements, Y is at least one metal selected from Group 3 (including the Lanthanides and Actinides) and Group 6 of the Periodic Table of Elements, and Z is at least one metal selected from Groups 7, 8, and 11 of the Periodic Table of Elements; m, n, p and q are the atomic ratios of their respective components and, when m is 1, n is from about 0.01 to about 0.75, p is from 0 to about 0.1, and q is the number of oxygen atoms necessary to satisfy the valence of the other components.

In another aspect, the invention resides in a process for selectively converting a dialkyl ether to the corresponding alkene and alkanol comprising contacting a feed containing at least one dialkyl ether with a catalyst comprising an acidic mixed metal oxide which comprises at least one metal selected from Group 4 of the Periodic Table of Elements and at least one metal selected from Group 3 (including the Lanthanides and Actinides) and Group 6 of the Periodic Table of Elements and which is produced by co-precipitating oxide precursors of the metals from a liquid medium and then calcining the co-precipitate.

Preferably, the at least one Group 4 metal comprises zirconium.

Preferably, the at least one metal selected from Group 3 and Group 6 comprises cerium, molybdenum, or tungsten, advantageously cerium.

Typically, the contacting is conducted at a temperature of about 50° C. to about 320° C., such as about 100° C. to about 275° C., or about 125° C. to about 250° C. Alternatively, in certain embodiments the contacting is conducted at a temperature of about 235° C. to about 290° C., such as about 235° C. to about 255° C., or about 254° C. to about 260° C., or about 250° C. to about 265° C. or about 250° C. to about 285° C. Typically the contacting is conducted at a pressure of about 0 kPa to about 3500 kPa, such as about 0 kPa to about 2400 kPa, or about 100 kPa to about 1400 kPa. Typically the contacting is conducted at a weight hourly space velocity (WHSV) of about 0.1 hr$^{-1}$ to about 250 hr$^{-1}$, such as about 0.5 hr$^{-1}$ to about 100 hr$^{-1}$.

In one aspect the invention resides in a process for the production of an alcohol from an olefin and water comprising (a) reacting the olefin and the water in the presence of an acidic catalyst under conditions sufficient to form a first crude alcohol stream comprising the water, the alcohol and a dialkyl ether; (b) separating the first crude alcohol stream into a water-alcohol mixture and a concentrated dialkyl ether stream; (c) contacting the concentrated dialkyl ether stream with a catalyst, the catalyst comprising a mixed metal oxide having the following composition $X_mY_nZ_pO_q$ where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p and q are the atomic ratios of their respective components and, when m is 1, n is from about 0.01 to about 0.75, p is from 0 to about 0.1, and q is the number of oxygen atoms necessary to satisfy the valence of the other components to form a crude dialkyl ether decomposition stream comprising the alcohol, the dialkyl ether, the olefin and the water; (d) removing at least a portion of the olefin from the crude dialkyl ether decomposition stream to form a substantially olefin-free dialkyl ether decomposition stream and a recovered olefin; (e) recycling at least a portion of the recovered olefin; (f) separating at least a portion of the dialkyl ether from the substantially olefin-free dialkyl ether decomposition stream to form a second crude alcohol stream; (g) recycling at least a portion of the dialkyl ether to step (c); and (h) recycling at least a portion of the second crude alcohol to the first crude alcohol stream.

Preferably, the at least one Group 4 metal comprises zirconium and the at least one metal selected from Group 3 and Group 6 comprises cerium, molybdenum, or tungsten, advantageously cerium.

In one aspect the invention resides in a process of improving the selectivity of olefin conversion in an olefin hydration process, the process comprising (a) contacting a dialkyl ether stream from the olefin hydration process with an ether decomposition catalyst, the ether decomposition catalyst comprising a mixed metal oxide having the following composition $X_mY_nZ_pO_q$ where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising an alcohol and an olefin; (b) recovering at least a portion of the olefin from the crude dialkyl ether decomposition stream; and (c) using at least a portion of the olefin recovered in step (b) in the olefin hydration process used to make the dialkyl ether decomposed in step (a).

In one aspect the invention relates to a process for the production of an alcohol comprising (a) reacting an olefin and water in the presence of a catalyst under conditions sufficient to form a crude alcohol stream comprising alcohol and a dialkyl ether; (b) separating at least a portion of the crude alcohol stream into an alcohol-containing stream and a dialkyl ether stream; (c) contacting at least a portion of the dialkyl ether stream with an ether decomposition catalyst, the ether decomposition catalyst comprising a mixed metal oxide having the following composition $X_mY_nZ_pO_q$ where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising alcohol and olefin; (d) recovering at least a portion of the olefin from the crude dialkyl ether decomposition stream; and (e) recycling at least a portion of the olefin recovered in step (d) to step (a). In one embodiment, the first mixture of olefins comprises at least two olefins having formulae $C_xH_{2x}$ and $C_yH_{2y}$, at least two alcohols having formulae $C_xH_{2x+1}OH$ and $C_yH_{2y+1}OH$, and at least two dialkyl ethers selected from formulae $C_xH_{2x+1}OC_xH_{2x+1}$, $C_yH_{2y+1}OC_yH_{2y+1}$, and $C_xH_{2x+1}OC_yH_{2y+1}$, and wherein x and y independently range from about 2 to about 10, alternatively from about 2 to about 3, and wherein x and y are not equal.

The process of the invention achieves the integration of an olefin hydration process to form an alcohol and the decomposition of by-product ethers to form alcohol and/or olefin which permits recycling of the olefin to obtain a high level of conversion of ethers to selectively produce the corresponding olefins and alcohols.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION

Introduction

Figure 1:
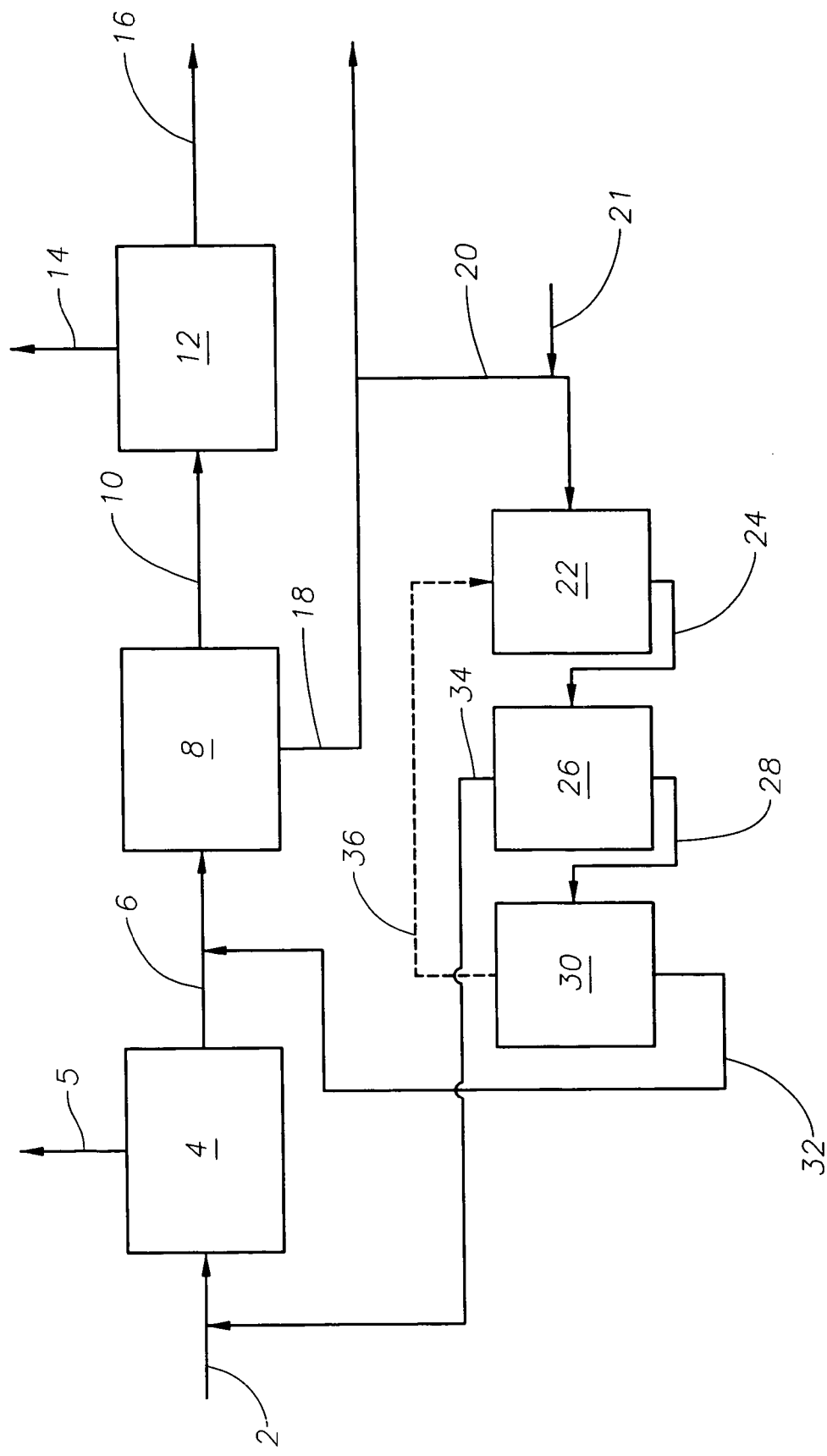
FIG. 1 is a block flow diagram of an integrated process using a distillation column.

The present invention is directed to an integrated process for the hydration of an olefin and the selective decomposition of by-product ethers to the corresponding olefins and alcohols. In one embodiment, the process converts dialkyl ether by-products, such as sec-butyl ether (SBE) and iso-propyl ether (IPE), also known as di-sec-butyl ether (DSBE) and di-isopropyl ether (DIPE), of olefin hydration reactions to higher value products, such as the olefin starting materials and alcohols. The recovered olefins from the ether decomposition are recycled to the hydration reactor. The alcohol from the ether decomposition is then sent to the alcohol purification step or distillation tower.

If the olefin hydration unit is feed limited, then the recovered olefin from an ether decomposition unit can serve as an additional feedstock source, which results in improving the overall net capacity of the olefin hydration process. If the olefin hydration process is not feed limited, the recovered olefin from the ether decomposition unit lowers the net raw material cost for the same level of production. The recovered olefin from the ether decomposition step typically has a higher purity than the base feedstocks for the olefin hydration process. The use of the recovered olefin permits a decrease in the usage rates of the other higher cost feedstocks that otherwise would normally feed the olefin hydration process. The use of recovered olefin permits the same level of alcohol production while also lowering the usage rates of the higher cost feeds, which lowers the raw material cost per pound of alcohol. The typical net raw material cost reduction is around 6% by recycling the recovered olefin versus purging.

Mixed Metal Oxide Catalyst Composition

The mixed metal oxide composition used as the catalyst in the processes of the invention comprises at least one first metal selected from Group 4 of the Periodic Table of Elements and at least one second metal selected from Group 3 (including the Lanthanides and Actinides) and Group 6 of the Periodic Table of Elements. It is to be appreciated that Periodic Table of Elements referred to herein is the IUPAC version described in the *CRC Handbook of Chemistry and Physics*, 78th Edition, CRC Press, Boca Raton, Fla. (1997).

Suitable Group 4 metals include titanium, zirconium and hafnium, with zirconium being most preferred. Suitable Group 3 metals include scandium, yttrium and lanthanum, and metals from the Lanthanide or Actinide series, such as cerium, praseodymium, neodymium, samarium, europium, gadolinium, terbium, dysprosium, holmium, erbium, thulium, ytterbium, lutetium and thorium. The most preferred Group 3 metal is cerium. Suitable Group 6 metals include chromium, molybdenum, and tungsten, with tungsten being most preferred. The first and second metal species present in the final catalyst are not limited to any particular valence state and may be present in any positive oxidation value possible for the respective species.

Other metals, such as metals of Groups 7, 8, and 11 of the Periodic Table of Elements, for example iron, manganese, and/or copper, may optionally be added to the present catalyst to alter its catalytic properties.

In one embodiment, the mixed metal oxide catalyst composition of the invention has the following empirical formula:

where X is at least one metal selected from Group 4 of the Periodic Table of Elements, Y is at least one metal selected from Group 3 (including the Lanthanides and Actinides) and Group 6 of the Periodic Table of Elements, and Z is at least one metal selected from Groups 7, 8, and 11 of the Periodic Table of Elements; m, n, p and q are the atomic ratios of their respective components and, when m is 1, n is from about 0.01 to about 0.75, such as from about 0.02 to about 0.6; p is 0 to about 0.1, such as from about 0 to about 0.05; and q is the number of oxygen atoms necessary to satisfy the valence of the other components. Thus in this embodiment, the mixed metal oxide compositions do not contain the silicon and/or aluminum present in the prior art catalysis disclosed in, for example, U.S. Pat. No. 5,171,920 and Japanese Published Patent Application No. JP-A-06072904.

The mixed metal oxide composition employed in the processes of the invention is produced by chemical interaction of a Group 4 metal oxide with an oxide or oxyanion of a Group 3 and/or 6 metal. The catalysts selected for the purposes of the present invention exhibit very high selectivity for ether decomposition, while minimizing side-reactions. While the authors do not wish to be bound by any theory, it seems that the selection of the particular metal elements and/or their relative ratios and/or the presence of sulfur, such as in specific amounts, provide acidic properties particularly well suited for ether decomposition.

The mixed oxides used in the processes of the present invention preferably contain sulfur, conveniently provided by the presence of sulfate ions in the precursor mixture. Sulfur is typically present in an amount of up to 5 wt. %, such as up to 1 wt. %, of the final mixed oxide composition.

The present mixed metal oxides may be composited with an inactive matrix material to form the finished form of the catalysts and for this purpose conventional matrix materials such as alumina and silica are suitable with preference given to silica as a non-acidic binder. Other binder materials may be used, for example, titania, zirconia and other metal oxides or clays. If a matrix is used, the active catalyst may be composited with the matrix in amounts from 90:10 to 10:90 by weight, e.g., from 80:20 to 20:80, or from 70:30 to 30:70 active catalyst:matrix. Compositing may be done by conventional means including mulling the materials together followed by extrusion or pelletizing into the desired finished catalyst particles.

Synthesis of the Mixed Metal Oxide Catalyst Composition

In one embodiment, the catalyst composition may be prepared by impregnation, for example by impregnation of a hydrothermally treated hydrated oxide of the Group 4 metal with an aqueous solution containing a source of ions of a Group 3 and/or Group 6 metal, followed by drying. The resulting catalyst precursor is then calcined in the manner described below.

In such an embodiment, a preferred source of the Group 4 metal oxide is hydrated zirconia. The expression, hydrated zirconia, is intended to connote a material comprising zirconium atoms covalently linked to other zirconium atoms via bridging oxygen atoms and further comprising available surface hydroxyl groups. Without being limited to any particular theory, the available surface hydroxyl groups are believed to react with the Group 3 and/or Group 6 species to form the present acidic catalyst component. Hydrated zirconia can be formed by precalcination of $Zr(OH)_4$ at a temperature of about 100° C. to about 400° C.

Preferably, the hydrated Group 4 metal oxide, such as hydrated zirconia, is subjected to an initial hydrothermal treatment to promote the interaction with the Group 3 and/or Group 6 metal species. The hydrothermal treatment conditions may include a temperature of at least 80° C., e.g., at least 100° C. The hydrothermal treatment may take place in a sealed vessel at greater than atmospheric pressure. However, a preferred mode of treatment involves the use of an open vessel under reflux conditions. Agitation of hydrated Group 4 metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of about 7 or greater, e.g., 9 or greater. Suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

Where the catalyst composition also contains a further metal selected from Groups 7, 8 and 11 of the Periodic Table of Elements, the further metal can be incorporated in the catalyst by impregnation at the same time as or separately from the impregnation with the Group 3 and/or Group 6 metal.

Suitable sources of ions of the Group 3 and/or Group 6 metal and the further metal include compounds such as oxychlorides, chlorides, alkoxides, sulfates and nitrates. Preferably, the Group 3 and/or Group 6 metal is present as a sulfate.

In another, more preferred embodiment, the catalyst is prepared by co-precipitation from a liquid mixture containing a source of Group 4 metal ions and a source of Group 3 and/or Group 6 metal ions followed by calcination of the resulting catalyst precursor in the manner described below. The liquid mixture can be prepared by combining a first liquid solution comprising a source of Group 4 metal ions with a second liquid solution comprising a source of Group 3 and/or Group 6 metal ions, wherein the combination takes place under conditions sufficient to cause co-precipitation of the catalyst precursor as a solid from the liquid medium. Alternatively, the source of the Group 4 metal ions and the source of the Group 3 and/or Group 6 metal ions may be combined into a single solution. This solution may then be subjected to conditions sufficient to cause co-precipitation of the catalyst, such as by the addition of a precipitating reagent, such as ammonium hydroxide, to the solution. Water is a preferred solvent for these solutions.

The pH at which the liquid mixture is maintained during co-precipitation appears to affect the activity of the final catalyst and hence the pH is preferably maintained at or below 9, such as between 3 and 9, for example between 6 and 9. The temperature at which the liquid mixture is maintained during the co-precipitation is generally less than about 200° C., such as from about 30° C. to about 100° C. The resulting gel is preferably then hydrothermally treated at temperatures of at least 80° C., preferably at least 100° C. The hydrothermal treatment typically takes place in a vessel at atmospheric pressure. The gel, in one embodiment, is hydrothermally treated for up to 10 days, such as up to 5 days, for example up to 3 days. The hydrated precursor to the metal oxide(s) is then recovered, for example by filtration or centrifugation, washed, dried and then calcined as described below.

Where the catalyst composition also contains a further metal selected from Groups 7, 8 and 11 of the Periodic Table of Elements, the further metal can be incorporated in the catalyst during coprecipitation of the oxide precursor of the Group 4 metal and the Group 3 and/or Group 6 metal.

Again, suitable sources of the metal ions for the coprecipitation include compounds such as oxychlorides, chlorides, alkoxides, sulfates and nitrates. Preferably, at least one of the metals is present as a sulfate and/or a source of sulfate ions is added to the liquid mixture from which the catalyst precursor is. precipitated. Where the Group 4 metal includes zirconium, the preferred source of zirconium is zirconium nitrate, and where the Group 3 metal includes cerium, the preferred source of cerium is a cerium sulfate.

Calcination of the catalyst precursor is effected, typically in an oxidizing atmosphere, at a temperature of at least 400° C., such as at least 500° C., for example from about 500° C. to about 800° C. The calcination time may be up to 48 hours, such as for about 0.5 to about 24 hours, for example for about 1 to about 10 hours. Where the catalyst precursor contains sulfate ions, the calcination conditions should be controlled so as to retain the desired sulfur level in the final catalyst composition.

Ether Decomposition Process

The ether decomposition process of the invention involves contacting an ether-containing feed with a mixed metal oxide catalyst described above under conditions effective to convert the ether to an olefin and an alcohol. Suitable ethers for use in the process of the invention include those having the formula

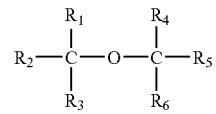

wherein $R_1$, $R_2$, $R_3$, $R_4$, $R_5$ and $R_6$ are the same or different and are selected from hydrogen, alkyl, arylalkyl and alkylaryl species each preferably having up to 20 carbon atoms. Alternatively, the dialkyl ether may have from about 2 to about 10 carbon atoms in each alkyl moiety, alternatively from about 2 to about 8 carbon atoms in each alkyl moiety, alternatively from about 2 to about 4 carbon atoms in each alkyl moiety, alternatively from about 3 to about 4 carbon atoms in each alkyl moiety. In one embodiment, the dialkyl ether comprises isopropyl ether, sec-butyl ether or mixtures thereof.

Although the dialkyl ethers used in the processes of the present invention are typically symmetrical, i.e., $R_1R_2R_3C$ is the same as $R_4R_5R_6C$, the present invention also encompasses unsymmetrical dialkyl ethers, i.e., $R_1R_2R_3C$ is different from $R_4R_5R_6C$. The unsymmetrical ether may arise from inadvertent or deliberate introduction of two or more olefins into the hydration step. For example, propylene used to make IPA may contain small amount of butenes. Typically $C_4$ olefins are present at less than about 1000 ppm, or less than about 5000 ppm. The hydration of a mixture of olefins can provide all combination of symmetrical and unsymmetrical olefins possible from the particular mixture of olefins.

The dialkyl ethers typically are essentially a single, symmetrical compound, but the processes of the present invention encompass mixtures of dialkyl ethers. The mixture of dialkyl ethers may result from using a mixture of olefins in the hydration step, which provides a mixture of symmetrical and unsymmetrical ethers. Alternatively a dialkyl ether may be prepared from hydration of a single olefin to provide a symmetrical ether and subsequent addition of one or more additional ethers, which may be symmetrical, unsymmetrical, or a mixture of symmetrical and unsymmetrical ethers.

In general, the conditions employed are not narrowly defined and depend not only on the ether starting material but also on the desired conversion rate and product selectivity. Typically, however, the conditions will include a temperature of about 50° C. to about 320° C., a pressure of about 0 kPa to about 3500 kPa, and a weight hourly space velocity (WHSV) of about 0.1 hr$^{-1}$ to about 250 hr$^{-1}$; such as a temperature of about 100° C. to about 275° C., a pressure of about 0 kPa to about 2400 kPa and a weight hourly space velocity (WHSV) of about 0.5 hr$^{-1}$ to about 10 hr$^{-1}$.

In a practical embodiment, the ether-containing feed contains isopropyl ether (IPE) and is produced as a by-product of propylene hydration, in a process for the manufacture of isopropyl alcohol (IPA). Some IPA processes involve contacting propylene with sulfuric acid. This can be accomplished with gas/liquid absorption or liquid/liquid extraction. While these processes have been utilized for several decades, some improvements have been made. The improvements include a process configuration that utilizes a unique combination of plug flow, bubble column, and closed stirred tank reactor reaction sections to achieve high conversion of dilute or concentrated propylene. Also spargers custom designed for the propylene/sulfuric acid absorption/extraction section can be used. Further, loop reactors may be preferred to improve mixing integrity.

One possible method of disposition of IPE produced as a side-product of IPA is as a fuel but, not only may this be subject to environmental regulation, but also a higher economic value can be achieved by selective decomposition of the IPE to propylene and IPA. The optimal pathway for this reaction is therefore shown by reaction (1):

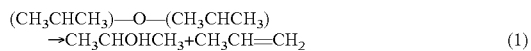
$$(CH_3CHCH_3)\text{—}O\text{—}(CH_3CHCH_3) \rightarrow CH_3CHOHCH_3+CH_3CH\text{=}CH_2 \quad (1)$$

The challenge faced in the catalytic decomposition of IPE is two-fold, firstly, minimizing the dehydration of IPA formed by reaction (1) to propylene according the reaction (2):

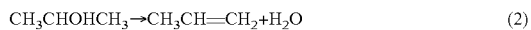
$$CH_3CHOHCH_3 \rightarrow CH_3CH\text{=}CH_2+H_2O \quad (2)$$

and secondly, minimizing oligomerization of the propylene formed according to reaction (3):

$$xCH_3CH\text{=}CH_2 \rightarrow (C_3H_6)_x \quad (3).$$

Although each of reactions (1)-(3) is acid catalyzed, the processes of the invention are effective to decompose IPE according to reaction (1) while reducing IPA dehydration and propylene oligomerization. Preferably, the conditions used to effect IPE decomposition include a temperature of about 100° C. to about 320° C., such as about 200° C. to about 300° C., for example about 210° C. to about 280° C.; a pressure of about 100 kPa to about 3550 kPa, such as about 400 kPa to about 1800 kPa, for example about 700 kPa to about 1500 kPa, a weight hourly space velocity (WHSV) of about 0.5 hr$^{-1}$ to about 250 hr$^{-1}$, such as about 3 hr$^{-1}$ to about 10 hr$^{-1}$, for example about 5 to 7 hr$^{-1}$ or 20 hr$^{-1}$ to 100 hr$^{-1}$, where the higher space velocities are preferred at higher temperature. Conveniently, the feed to the catalyst includes water in addition to the IPE, with the molar ratio of water to IPE typically ranging from 0 to 3, such as about 0.5 to about 2, for example about 0.7 to 1.5.

In yet another practical embodiment, the ether-containing feed contains sec-butyl ether (SBE) and is produced as a by-product of the hydration of butene to produce sec-butanol. One possible method of disposition of the SBE is as a fuel, for example by addition to motor vehicle gasoline, but, not only may this be subject to environmental regulation, it also leads to a loss of butenes as a lower-valued component. Moreover, the SBE may not be readily isolatable as a single component stream by conventional separation techniques, and may form a mixture with close-boiling butene oligomers composed mostly of $C_8$ olefins formed by dimerization of the butenes. However, while the $C_8$ olefins, being highly branched, would make a good high-octane additive to gasoline, environmental regulation may require elimination of the SBE from this stream. Accordingly, a preferred decomposition pathway for SBE is by conversion to sec-butanol and 2-butene in a process that limits oligomerization of the butene formed and of the $C_8$ olefins present.

The catalyst compositions of the present invention are active for the selective conversion of SBE to sec-butanol and 2-butene with limited oligomerization of the resultant butenes and limited oligomerization/isomerization of any $C_8$ olefins present. At higher temperatures, some or all of the sec-butanol may be dehydrated to 2-butene according to a reaction of the type indicated above as reaction (2). In this embodiment, preferred ether decomposition conditions include a temperature of about 150° C. to about 275° C. a pressure of about 0 kPa to about 700 kPa, and a weight hourly space velocity (WHSV) of about 0.5 hr$^{-1}$ to about 10 hr$^{-1}$. Conveniently, the feed to the catalyst includes water in addition to the SBE, with the molar ratio of water to SBE typically ranging from 0 to 3, such as about 0.5 to about 2, for example about 0.7 to 1.5.

The processes of the invention may be conducted in a stationary or fluidized bed, and may take place continuously or batch-wise.

The processes of the invention may be conducted using pure ether feedstocks, or they may include a diluent such as nitrogen, argon, carbon dioxide, alkanes, and the like. In a preferred embodiment, water may be added together with the ether feed to minimize dehydration of the resultant alcohols.

Integrated Olefin Hydration and Ether Decomposition

The integrated olefin hydration and ether decomposition is discussed with reference to FIGS. 1 and 2. The integrated process may be used for any of the embodiments described above. The following description of certain embodiments exemplifying IPA/IPE is illustrative only and not limiting.

The olefin hydration may be any conventional process, including direct hydration and indirect hydration, which are well known. Indirect hydration is typically accomplished by contacting an olefin, for example propylene, with a strong mineral acid such as sulfuric acid or phosphoric acid in the presence of water. The propylene reacts with the acid to form an isopropyl sulfate ester and/or diester or phosphate equivalent. This isopropyl sulfate ester is then hydrolyzed by the injection of water to form IPA and the mineral acid. The major by-product of these processes is the corresponding ether, for example IPE, which can be formed at up to about 15 weight % by weight of the IPA produced. Examples of indirect hydration of olefins are disclosed in U.S. Pat. Nos. 4,471,142 and 4,296,261, which are incorporated by reference.

In one embodiment, the indirect hydration process operates at a pressure ranging from about 50 psig (345 kPag) to about 500 psig (3448 kPag), a temperature ranging from about 65° C. to about 120° C., a WSV ranging from about 0.2 hr$^{-1}$ to about 0.8 hr$^{-1}$, a water to alcohol molar ratio ranging from about 1 to about 4, and the catalyst selected from sulfuric acid and phosphoric acid.

Direct hydration processes typically use solid acid catalyst or heterogeneous catalyst for the hydration of the propylene directly to IPA. In the direct process, the hydration of the olefins to alcohols is carried out directly and in a single step, by contacting the olefin with the hydration water in the presence of an acidic catalyst. Direct hydration processes typically require chemical grade propylene or higher to decrease impurities produced and maintain catalyst life. Direct hydration may be carried out in vapor-phase, liquid-phase or mixed phase. IPE is also the major by-product from direct hydration processes but usually it forms in lower amounts than indirect hydration processes. Examples of indirect hydration of olefins are disclosed in U.S. Pat. Nos. 4,469,903 and 4,456,776, which are incorporated by reference.

In one embodiment, the direct hydration process typically operates at a pressure ranging from about 200 psig (1379 pKa) to about 2000 psig (13,790 kPa), a temperature ranging from about 80° C. to about 180° C., a WHSV ranging from about 0.1 hr$^{-1}$ to about 5 hr$^{-1}$, a water to alcohol molar ratio ranging from about 0.1 to about 20, and the catalyst selected from acid catalysts such as acidic resins, solid phosphoric acid (SPA) catalysts, acidic zeolites, solid metal oxide catalysts, mixed metal oxides, and silicotungstate catalysts.

Further details regarding direct and indirect hydration processes may be found in Industrial Organic Chemistry, 2nd Revised and Extended Edition, Section 8.1.2, pp. 194-97 (1993) by K. Weisselmel and H.-J. Arpe, which is incorporated by reference.

Figure 2:
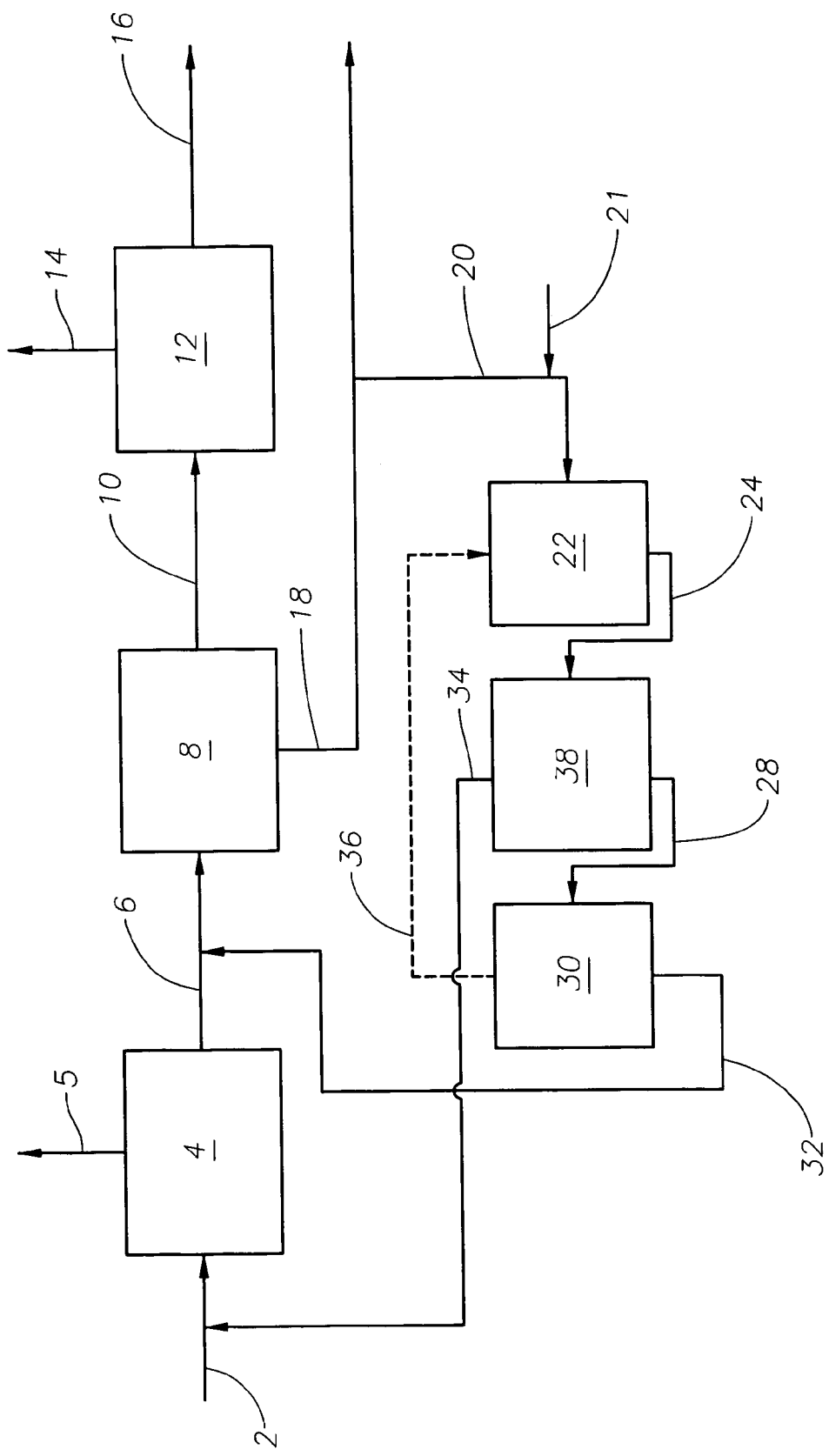
FIG. 2 is a block flow diagram of an integrated process using a flash drum and compressor separation.

Typically, the hydration process, shown in FIGS. 1 and 2, includes feeding an olefin/alkane mixture, such as propylene/propane, via line 2 into an olefin hydration unit 4. The propylene is treated in a direct or indirect hydration unit 4 with an acid, such as sulfuric acid, in the presence of water with propane venting via line 5, to form a crude IPA stream comprising IPA, IPE and water. The crude IPA stream is transferred via line 6 to an IPA purification unit 8, which includes, but is not limited to, a distillation tower 26. The IPA purification unit 8 separates the crude IPA stream into a water-IPA azeotrope and a concentrated IPE stream. The water-IPA azeotrope is transferred via line 10 to an IPA drying column 12 that removes water via line 14 and provides IPA typically having a purity of about 99.9 weight % via line 16.

In a conventional IPA process, the concentrated IPE stream, comprising IPE, IPA and water, is transferred via line 18 to a receiving vessel, not shown, to be blended with gasoline to serve as an oxygenate. In one embodiment of the present invention the concentrated IPE stream is transferred via lines 18 and 20 to an ether decomposition system comprising an ether decomposition reactor 22, a flash drum and condenser 38 and a wash tower 30.

In one embodiment concentrated IPE stream from line 18 enters line 20, which is connected to line 21 to provide additional water. The concentrated IPE stream and co-injected water, if any, which is vaporized upon entering the ether decomposition unit 22, which has a fixed bed reactor of the mixed metal oxide catalyst described above. In one embodiment, the mixed metal oxide catalyst comprises CeO/ZrO$_2$. In one embodiment, the ether decomposition reactor typically operates at a pressure ranging from about 50 psig (345 kPag) to about 500 psig (3448 kPag), preferably from about 50 psig (345 kPag) to about 200 psig (1379 kPag), more preferably from about 90 psig (621 kPag) to about 200 psig (1379 kPag), and yet more preferably about 120 psig (827 kPag) to about 200 psig (1379 kPag). In one embodiment the ether decomposition reactor operates at a temperature ranging from about 50° C. to about 320° C., preferably from about 100° C. to about 320° C., more preferably from about 235° C. to about 285° C. In one embodiment the ether decomposition reactor operates at a throughput rate ranging from about 1 to about 20 hr$^{-1}$. In one embodiment, the ether decomposition reactor operates at a WHSV ranging from about 0.1 hr$^{-1}$ to about 250 hr$^{-1}$, or from about 0.5 hr$^{-1}$ to about 100 hr$^{-1}$, or from about 1 hr$^{-1}$ to about 100 hr$^{-1}$, or from about 2 hr$^{-1}$ to about 100 hr$^{-1}$. In one embodiment, the ether decomposition reactor provides an alcohol yield per pass ranging from about 40 weight % to about 60 weight % or from about 20 weight % to about 69 weight % based on the ether. In another embodiment, the ether decomposition reactor operates at a water to ether molar ratio ranging from about 0.5 to about 2.0 or from about 0.5 to about 2.5 or from about 0.1 to about 3.0. The relatively low amount of added water, compared to other methods of ether decomposition, reduces the amount of water that must be removed from the IPA, which increases the productivity of the process with respect to the IPA.

In one embodiment, the ether decomposition unit 22 provides the distillation tower 26 with a feed stream, via line 24, comprising water, IPE, and propylene and IPA, from cracking IPE. The propylene is separated in the distillation tower 26 and recycled, via line 34, to the hydration unit 4 via the propylene/propane feed line 2. In one embodiment, the distillation tower 26 typically operates at a pressure ranging from 0 psig (0 kPag) to about 200 psig (1379 kPag), preferably at a pressure greater than about 150 psig (1034 kPag). In another embodiment, the distillation tower 26 typically operates at a pressure ranging from about 0 psig (0 kPag) to about 500 psig (3448 kPag), or from about 50 psig (345 kPag) to about 250 psig (1724 kPag), or from about 150 psig (1034 kPag) to about 210 psig (1448 kPag). In one embodiment, the distillation tower 26 typically operates at a temperature ranging from about 30° C. to about 190° C. depending on the pressure used.

A bottom stream from the distillation tower 26 comprising IPE, IPA and water is fed via line 28 to a wash tower 30 in which a liquid/liquid extraction with water removes the IPA. The IPA-water wash is typically recycled via line 32 to the line 6, which conveys crude IPA to the IPA purification unit 8. The IPE is removed overhead from the wash tower 30 via line 36 to recycle the IPE to the ether decomposition unit 22.

In one embodiment, the distillation tower 26 typically provides high purity propylene having a purity greater than 95 weight %, preferably greater than 98 weight %, more preferably greater than 99 weight % and yet more preferably greater than 99.9 weight %. This propylene typically does not require further purification before recycling to the hydration unit 2. The high purity of the propylene from the distillation tower 26 permits the integration of the ether decomposition process into the propylene hydration process.

In another embodiment, as shown in FIG. 2, the ether decomposition system comprises an ether decomposition unit 22, a flash drum and condenser 38, instead of a distillation tower 26, and a wash tower 30. The ether decomposition unit 22 and the wash tower 32 are generally operated the same as for the embodiment described above having a distillation tower 26. The flash drum and condenser 38 is typically operated at a pressure less than about 100 psig (690 kPag) or less than about 150 psig (1034 kPag) or less than about 180 psig (1241 kPag). The propylene is condensed to a liquid form and recycled via line 34 to the hydration unit 4.

Table 4 shows typical, i.e., non-limiting, operating conditions for an ether decomposition reactor 22 processing IPE using a catalyst having about 17 weight % cerium based on the total weight of the CeO/ZrO$_2$ catalyst. Table 4 exemplifies certain embodiments of the present invention using either the distillation tower 26 or the flash drum and condenser 38.

In one embodiment, an aspect of the invention relates to a process for the production of an alcohol, the process comprising (a) reacting an olefin and water in the presence of a catalyst under conditions sufficient to form a crude alcohol stream comprising alcohol, and a dialkyl ether; (b) separating at least a portion of the crude alcohol stream into an alcohol-containing stream and a dialkyl ether stream; (c) contacting at least a portion of the dialkyl ether stream with an ether decomposition catalyst, the ether decomposition catalyst comprising a mixed metal oxide having the following composition $X_m Y_n Z_p O_q$ where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising alcohol and olefin; (d) recovering at least a portion of the olefin from the crude dialkyl ether decomposition stream; and (e) recycling at least a portion of the olefin recovered in step (d) to step (a).

In another embodiment an aspect of the invention relates to the process wherein the crude dialkyl ether decomposition stream comprises residual dialkyl ether, and the process further comprises the step of recycling at least a portion of the residual dialkyl ether to step (c). In another embodiment an aspect of the invention relates to the process wherein at least a portion of the alcohol from the crude dialkyl ether decomposition stream is combined with the alcohol obtained at step (b).

In another embodiment an aspect of the invention relates to a process of improving the selectivity of olefin conversion in an olefin hydration process, the process comprising (a) contacting a dialkyl ether stream from the olefin hydration process with an ether decomposition catalyst, the ether decomposition catalyst comprising a mixed metal oxide having the following composition $X_m Y_n Z_p O_q$ where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising an alcohol and an olefin; (b) recovering at least a portion of the olefin from the crude dialkyl ether decomposition stream; and (c) using at least a portion of the olefin recovered in step (b) in the olefin hydration process used to make the dialkyl ether decomposed in step (a). In one embodiment another aspect of the invention relates to a process for the production of alcohols by dialkyl ether decomposition, the process comprising (a) reacting a mixture of olefins and water in the presence of a catalyst under conditions sufficient to form a first crude mixed alcohol stream comprising the water, a first mixture of alcohols, and a first mixture of dialkyl ethers; (b) recovering at least a portion of the first mixture of dialkyl ethers; (c) contacting at least a portion of the first mixture of dialkyl ethers recovered at step (b) with an ether decomposition catalyst, the ether decomposition catalyst comprising a mixed metal oxide having the following composition $X_m Y_n Z_p O_q$ where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising a second mixture of alcohols and a second mixture of olefins; (d) recovering at least a portion of the second mixture of olefins from the first crude dialkyl ether decomposition stream; and (e) recycling at least a portion of the olefins recovered in step (d) to step (a). In another embodiment another aspect of the invention relates to the process wherein the crude dialkyl ether decomposition stream comprises at least one dialkyl ether, and the process further comprises the step of recycling at least a portion of the at least one dialkyl ether to step (c). In another embodiment an aspect of the invention relates to the process wherein at least a portion of the second mixture of alcohols from the crude dialkyl ether decomposition stream is combined with at least a portion of the first mixture of alcohols. In one embodiment an aspect of the invention relates to the process wherein the first mixture of olefins comprises at least two olefins having formulae $C_x H_{2x}$ and $C_y H_{2y}$, at least two alcohols having formulae $C_x H_{2x+1} OH$ and $C_y H_{2y+1} OH$, and at least two dialkyl ethers selected from formulae $C_x H_{2x+1} OC_x H_{2x+1}$, $C_y H_{2y+1} OC_y H_{2y+1}$, and $C_x H_{2x+1} OC_y H_{2y+1}$, and wherein x and y independently range from about 2 to about 10, alternatively from about 2 to about 4 and wherein x and y are not equal. This embodiment of the processes of the present invention may operate under the conditions described above for other embodiments.

In yet another embodiment, the invention relates to a process for the production of an alcohol from an olefin and water, the process comprising (a) reacting the olefin and the water in the presence of a catalyst under conditions sufficient to form a first crude alcohol stream comprising the alcohol, the water and a dialkyl ether; (b) separating the first crude alcohol stream into a water-alcohol mixture and a dialkyl ether stream; (c) contacting at least a portion of the dialkyl ether stream with an ether decomposition catalyst to form a crude dialkyl ether decomposition stream comprising the alcohol, residual dialkyl ether, the olefin and the water, wherein a molar ratio of the water to the residual dialkyl ether is less than 3.0; (d) recovering at least a portion of the olefin from the crude dialkyl ether decomposition stream; (e) recycling at least a portion of the olefin recovered in step (d) to step (a); (f) recovering at least a portion of the dialkyl ether from the crude dialkyl ether decomposition stream to form a second dialkyl ether stream and a second crude alcohol stream; (g) recycling at least a portion of the second dialkyl ether stream to step (c); and (h) combining at least a portion of the second crude alcohol stream with the first crude alcohol stream.

The invention will now be more particularly described with reference to the following non-limiting Examples. Unless otherwise stated, all percentages are weight percent. The pH in the following examples was adjusted to the desired pH with the addition of either concentrated sulfuric acid or concentrated ammonium hydroxide depending on the initial pH of the gel.

EXAMPLES

Figure 3:
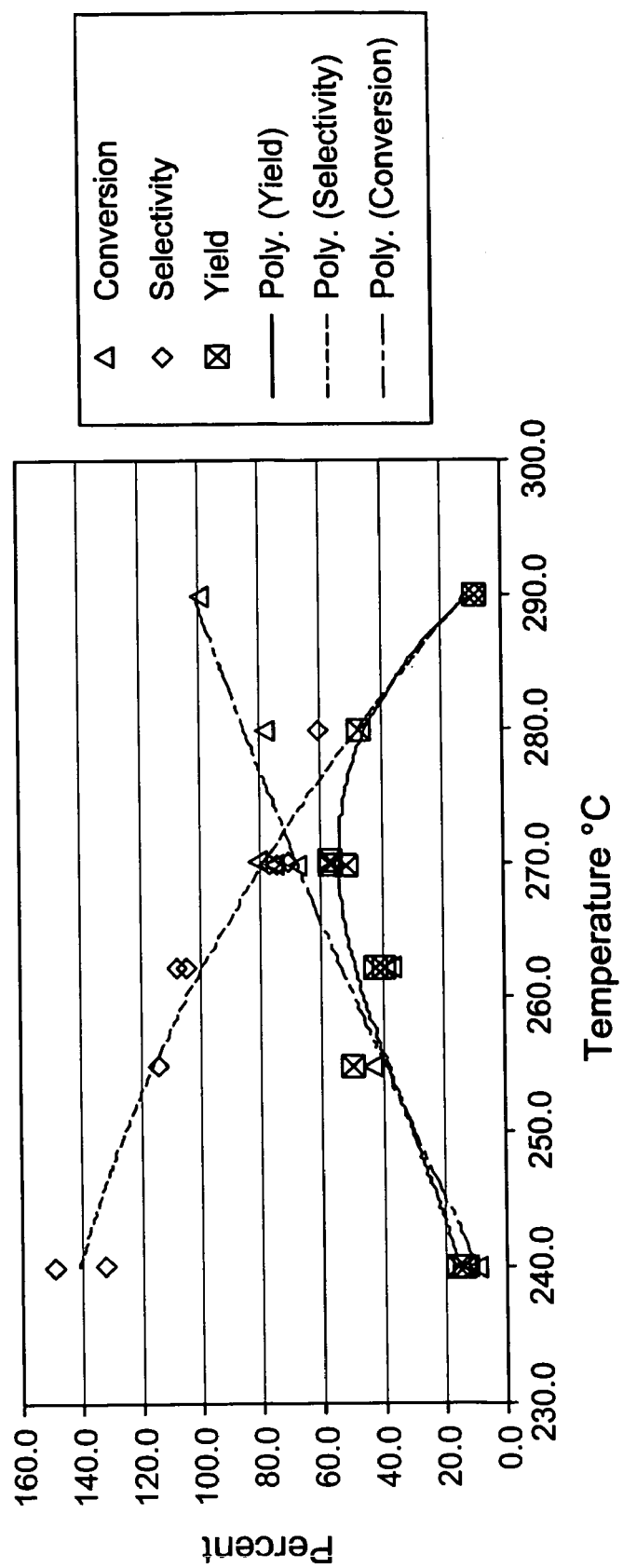
FIG. 3 shows yield per pass versus temperature at 200 psig (1379 kPag).
Figure 4:
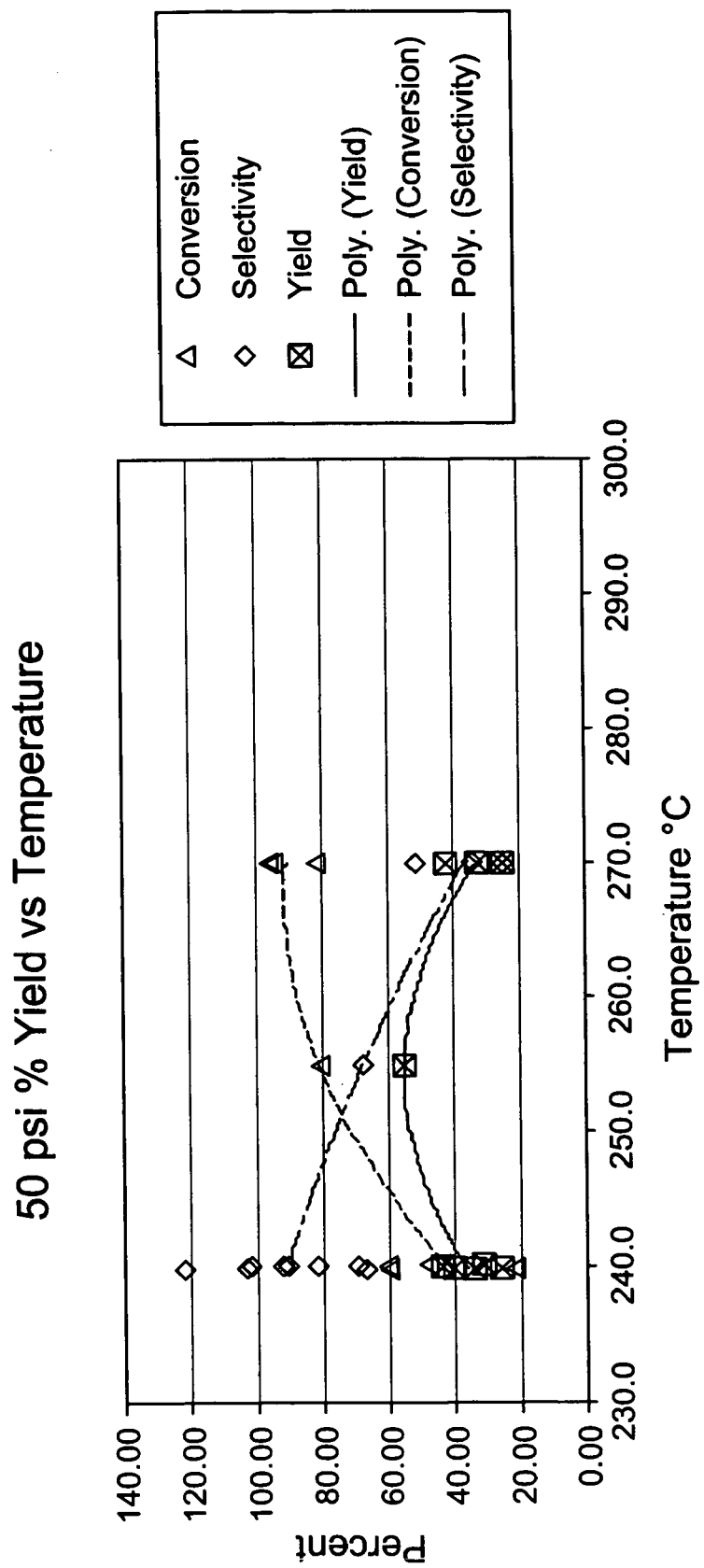
FIG. 4 shows yield per pass versus temperature at 50 psig (345 kPag).
Figure 5:
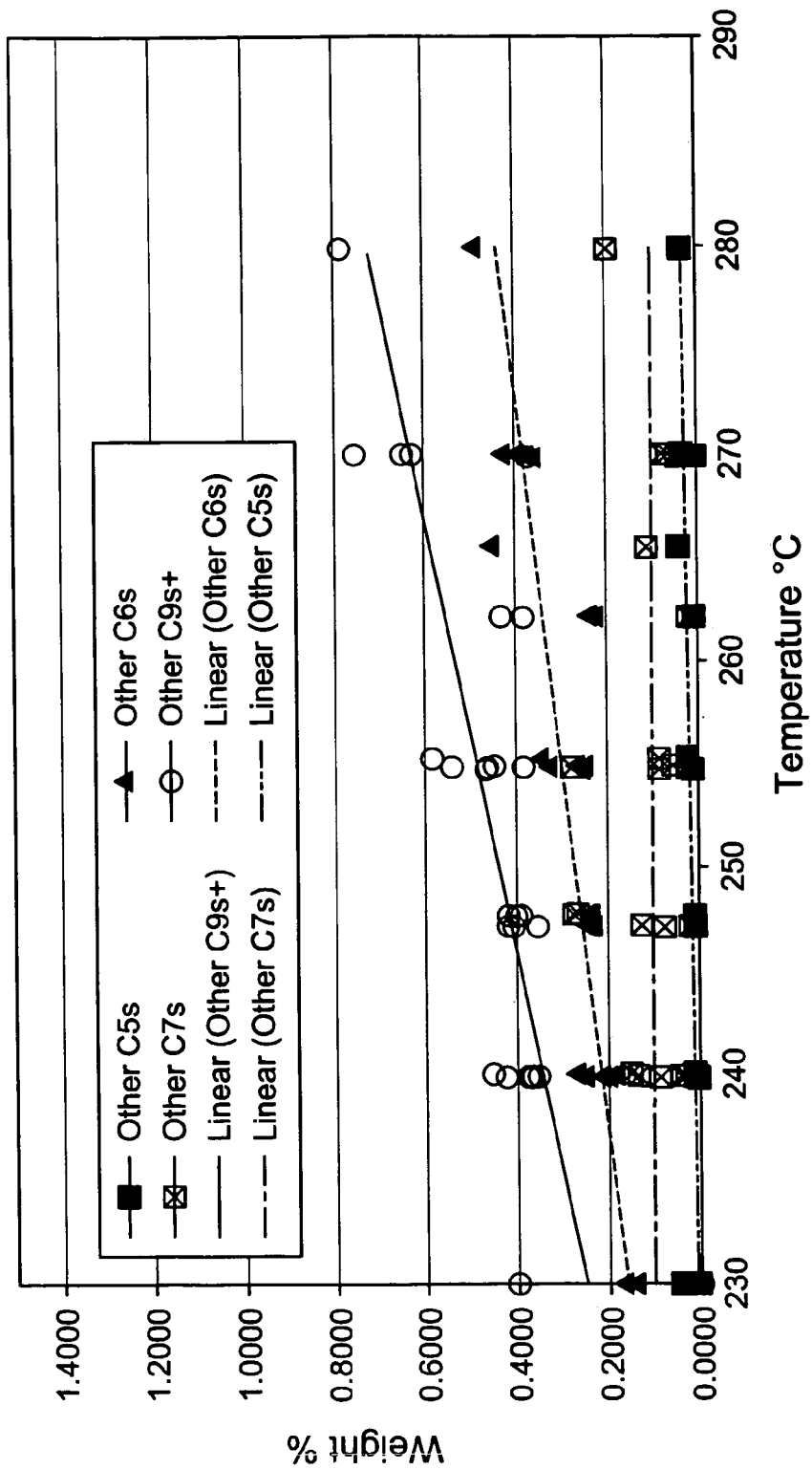
FIG. 5 shows the weight % of heavy impurities as a function of temperature.

The data sets plotted in FIGS. 3, 4, and 5 have been modeled using a polynomial regression technique to provide easily viewed trend lines of the data. All pressures in kPag units were calculated by multiplying the psig values by a conversion factor of 6.895, which means all kPag pressures are gauge pressures, not absolute pressures.

Example 1

Synthesis of $Ce/ZrO_2$ (30 wt. % Ce)

One hundred and twenty-five grams of $ZrOCl_2 \cdot 8H_2O$ and 52 grams of cerium sulfate were dissolved with stirring in 1.5 liters of distilled water. Another solution containing 65 gram of concentrated $NH_4OH$ and 1.5 liters of distilled water was prepared. These two solutions were combined at room temperature at the rate of 50 ml/min using a nozzle mixer. The pH of this combined mixture was adjusted to 8 with the addition of concentrated sulfuric acid ($H_2SO_4$). This slurry was then put in polypropylene bottles and placed in a steambox (100° C.) for 72 hours. The product formed was recovered by filtration, washed with excess water, and dried overnight at 85° C. The composition of the product was analyzed using X-ray fluorescence. The elemental analysis for the as-synthesized material was: Ce—26 weight %, Zirconium—47 weight %, and Sulfur—1.54 weight percent, corresponding to a mixed metal oxide of formula $Zr_m Ce_n O_q S_r$ in which m=1.0, n=0.36 and r=0.19. A portion of this material was calcined to 700° C. in flowing air for 3 hours to produce a solid containing a nominal 30% Ce on zirconia. Elemental analyses indicated that the cerium content was 26% by weight.

Example 2

IPE Decomposition over $Ce/ZrO_2$

The decomposition of isopropyl ether (IPE) was investigated in a fixed-bed microreactor. 0.5 gram of the calcined catalyst of Example 1 was loaded into a stainless steel reactor having an outside diameter of 0.375 inch (9.5 mm) and was dried with $N_2$ at 200° C. Isopropyl ether (99%, Aldrich) was fed to the reactor at a WHSV of 6 $hr^{-1}$. Reactor pressure was atmospheric. Products were analyzed by on-line Gas Chromatography. Table 1 summarizes the performance of the catalyst, at different reaction temperatures, using the following definitions:

TABLE 1

IPE Decomposition over $Ce/ZrO_2$

| Product Composition (wt. %) | Temperature (° C.) | |
|---|---|---|
| | 200 | 210 |
| | Time on Stream (hr) | |
| | 21 | 61 |
| Propylene | 41.06 | 55.69 |
| Isopropanol | 31.09 | 27.21 |
| Isopropyl ether | 24.16 | 10.00 |
| $C_6$'s | 0.07 | 0.09 |
| $C_9$'s | 0.03 | 0.00 |
| $C_{12}$'s | 0.00 | 0.00 |
| Water | 3.55 | 6.96 |
| IPE Conversion (%) | 75.8 | 90.0 |
| IPA Conversion (%) | 30.3 | 48.6 |
| Propylene Selectivity (%) | 99.7 | 99.8 |
| IPA Selectivity (%) | 69.8 | 51.4 |
| IPA Yield | 52.9 | 46.3 |

IPE Conversion = $(IPE_{product} - IPE_{feed})/IPE_{feed}$ where $IPE_{product}$ is the wt.% of IPE in the product and where $IPE_{feed}$ is the wt.% of IPE in the feed;
IPA Conversion = $(IPA_{theoretical} - IPA_{product})/(IPA theoretical)$ where $IPA_{theoretical}$ = theoretical IPA produced stoichiometrically from the IPE decomposed; where $IPA_{product}$ is the wt.% of IPA in the product;
IPA Selectivity = $IPA_{product}/(IPA_{theoretical})$
IPA Yeild (per pass) = IPE Conversion × IPA Selectivity.

As the data of Table 1 show, the ceria-zirconia catalyst achieves high conversion of IPE with low conversion of IPA. Production of propylene dimers and trimers is low, with exit concentrations on the order of 800 ppm for the dimer.

By raising the temperature, it is possible to achieve full conversion of IPE, but this comes at the cost of increased conversion of IPA to propylene. The advantages of full conversion of IPE to propylene include a reduction in separation complexity of the resulting stream, as propylene can be more readily separated using a flash drum or distillation column and recycled back to the isopropanol manufacturing process.

Example 3

SBE Decomposition over 30% $Ce/ZrO_2$

The decomposition of sec-butyl ether (SBE) was investigated on the calcined $Ce/ZrO_2$ catalyst prepared at Example 1. The procedure described at Example 2 was followed except a feed stream containing 53.4% sec-butyl ether (SBE), with the balance being mostly C8 olefins, was fed to the reactor at a WHSV of 5 $hr^{-1}$. Reactor pressure was 50 psig (345 kPag). Products were analyzed by on-line Gas Chromatography. Table 2 summarizes the conversion of SBE, the conversion of SBA and the butane selectivities at different reaction temperatures.

TABLE 2

SBE Decomposition over 30% $Ce/ZrO_2$

| Product Composition | Temperature (° C.) | | |
|---|---|---|---|
| | 200 | 210 | 220 |
| | Time on Stream (hr) | | |
| | 23 | 47 | 65 |
| 1-butene | 0.60 | 0.63 | 0.65 |
| Isobutene | 2.38 | 3.24 | 3.91 |
| Trans-2-butene | 12.96 | 16.96 | 18.96 |
| Cis-2-Butene | 11.33 | 15.11 | 17.00 |
| Sec-Butanol | 11.13 | 5.78 | 2.00 |

TABLE 2-continued

SBE Decomposition over 30% Ce/ZrO$_2$

|  | Temperature (° C.) | | |
|---|---|---|---|
|  | 200 | 210 | 220 |
|  | Time on Stream (hr) | | |
| Product Composition | 23 | 47 | 65 |
| SBE | 8.80 | 1.31 | 1.26 |
| Total C$_8$ olefins | 48.83 | 50.49 | 48.69 |
| Water | 3.33 | 5.72 | 6.69 |
| SBE Conversion (%) | 83.5 | 97.6 | 97.6 |
| SBA Conversion (%) | 56.2 | 80.5 | 93.3 |
| SBA Selectivity (%) | 43.7 | 19.4 | 6.7 |

As the data of Table 2 show, raising the temperature promotes higher conversion of SBE using the ceria zirconia catalyst. Analysis of the C$_8$ isomers showed that the concentrations of the 2,3-dimethyl-1-hexene and 2,3,3-trimethyl-1-pentene did not vary significantly with time on-stream or temperature, suggesting that there is little isomerization taking place among these isomers.

Example 4

Synthesis of Ce/ZrO$_2$ (24 wt. % Ce)

A Ce/ZrO$_2$ mixed oxide catalyst having a nominal 24% Ce on zirconia was prepared by a procedure similar to that of Example 1. The elemental analysis of the as-synthesized material was: Ce—23.2 weight %, Zirconium—46.3 weight %, and Sulfur—2.82 weight percent, corresponding to a mixed metal oxide of formula Zr$_m$Ce$_n$O$_q$S$_r$ in which m=1.0, n=0.33 and r=0.35. A portion of this material was calcined to 700° C. in flowing air for 3 hours to produce a solid containing a nominal 24% Ce on zirconia.

Example 5

SBE Decomposition and SBA Recovery over 24% Ce/ZrO$_2$

The decomposition of SBE and recovery of SBA were investigated for the Ce/ZrO2 catalyst of Example 4. The procedure of Example 3 was followed except water (HPLC grade, Aldrich Chemical Company) was co-fed to the reactor at a SBE/H$_2$O molar ratio of 1.0. Reactor pressure was 50 psig (345 kPag). Products were analyzed by on-line Gas Chromatography. Table 3 summarizes the conversion of SBE, the conversion of SBA, and the butane selectivities, at different reaction temperatures.

TABLE 3

SBE Decomposition and SBA Recovery over 24% Ce/ZrO$_2$

|  | Temperature (° C.) | |
|---|---|---|
|  | 200 | 210 |
|  | Time on Stream (hr) | |
| Product Composition (wt. %) | 53 | 65 |
| 1-butene | 0.54 | 0.55 |
| Isobutene | 1.17 | 1.87 |
| Trans-2-butene | 6.27 | 9.47 |
| Cis-2-Butene | 5.47 | 9.00 |
| Sec-Butanol | 8.19 | 15.37 |
| SBE | 23.90 | 7.81 |
| Total C$_8$ olefins | 45.38 | 46.29 |
| Water | 8.58 | 9.08 |
| SBE Conversion (%) | 51.6 | 84.2 |
| SBA Conversion (%) | 43.6 | 35.1 |
| SBA Selectivity (%) | 56.4 | 64.8 |

The data of Table 3 show that co-feeding water suppresses the dehydration of SBA to butene, thereby increasing the selectivity towards SBA.

Example 6

Decomposition of Commercial IPE in Pilot Plant Testing

The decomposition of isopropyl ether (IPE) was investigated in a pilot plant with a fixed-bed reactor. 40 grams of a calcined catalyst similar to the catalyst of Example 1, except that the cerium loading was 17 wt. %, was loaded into the pilot plant reactor and was dried with N$_2$ at 200° C. Isopropyl ether, from a commercial IPA manufacturing process, was fed to the reactor under conditions shown in Table 4. The feed IPE composition was about 93 wt. % IPE, less than 1 wt. % water, about 5 wt. % IPA, with the remainder including C$_6$ hydrocarbons compounds, and light oxygenates including n-propyl alcohol and ketones. Water was added as needed to provide the desired water to IPE ratio. Products were analyzed by on-line Gas Chromatography. Table 4 summarizes the performance of the catalyst at different reaction temperatures, pressure, WHSV, and water to IPE molar ratio.

TABLE 4

IPA Yield versus Reactor Conditions

| Pressure psig/kPag | Temperature ° C. | WHSV hr$^{-1}$ | H$_2$O/IPE molar ratio | IPA Yield per pass wt % |
|---|---|---|---|---|
| 50/345 | 235–255 | 1–5 | 0.5–1.2 | 40–60 |
| 90/621 | 240–260 | 3–5 | 0.8–1.2 | 40–60 |
| 120/827 | 250–265 | 3–7 | 0.8–1.2 | 40–60 |
| 200/1379 | 250–285 | 5–9 | 0.8–2.0 | 40–60 |

The FIGS. 3 and 4 show yields per pass versus temperature data. The data for the 200 psig (1379 kPag) exemplifies an ether decomposition reacting under conditions in which a distillation tower 26 would be useful. The data for the 50 psig (345 kPag) exemplifies an ether decomposition reacting under conditions in which a flash drum and condenser would be useful. The data for FIGS. 3 and 4 are in Tables 12 and 13.

In Tables 5 and 6, the IPE conversion is calculated based on the difference of the weight of IPE in the feed and the weight of IPE in the product and assumes that one mole of IPE is converted to one mole of IPA and one mole of propylene. The IPA selectivity in some cases exceeds 100% since this value is based on the moles of IPA in the product divided by the difference in the number of moles of IPE in the feed and the number of moles in the products. However, since some IPE can also decompose by hydration of the IPE to give two moles of IPA and no propylene, this hydration of IPE can result in the IPA selectivity exceeding 100%. The IPA wt. % yield is calculated by multiplying the IPA conversion and the IPA selectivity.

TABLE 5

200 PSIG Data for IPA Wt. % Yield Per Pass versus Temperature

| Item | Temperature °C. | IPE Conversion Wt. % | IPA Selectivity | IPA Yield Wt. % |
|---|---|---|---|---|
| 1 | 269.9 | 67.9 | 76.8 | 52.1 |
| 2 | 240.0 | 11.9 | 132.7 | 15.8 |
| 3 | 280.0 | 78.8 | 60.7 | 47.8 |
| 4 | 270.1 | 80.7 | 70.7 | 57.0 |
| 5 | 254.9 | 43.3 | 115.0 | 49.8 |
| 6 | 270.1 | 79.2 | 71.5 | 56.6 |
| 7 | 240.1 | 9.61 | 148.5 | 14.3 |
| 8 | 262.1 | 37.0 | 108.0 | 40.0 |
| 9 | 290.0 | 99.3 | 8.8 | 8.7 |
| 10 | 262.2 | 40.2 | 105.2 | 42.3 |
| 11 | 270.0 | 75.6 | 74.9 | 56.6 |

TABLE 6

50 PSIG Data for IPA Wt. % Yield Per Pass versus Temperature

| Item | Temp. C.° | IPE Conversion Wt. % | IPA Selectivity | IPA Yield Wt. % |
|---|---|---|---|---|
| 1 | 240.0 | 60.0 | 70.0 | 42.0 |
| 2 | 239.9 | 59.9 | 67.0 | 40.1 |
| 3 | 239.9 | 21.7 | 122.1 | 26.5 |
| 4 | 240.1 | 45.7 | 92.2 | 42.2 |
| 5 | 240.0 | 47.6 | 91.2 | 43.4 |
| 6 | 240.0 | 32.6 | 101.7 | 33.1 |
| 7 | 255.0 | 81.0 | 67.6 | 54.8 |
| 8 | 270.0 | 81.4 | 51.7 | 42.0 |
| 9 | 240.0 | 37.8 | 81.7 | 30.9 |
| 10 | 239.9 | 32.4 | 103.9 | 33.6 |
| 11 | 270.0 | 94.6 | 33.6 | 31.8 |
| 12 | 270.1 | 96.5 | 25.0 | 24.2 |

The data in Tables 5 and 6, see FIGS. 3 and 4, show the relationship of temperature to conversion and selectivity for the decomposition of IPE. As the either decomposition temperature increases, the conversion of the ether decomposition increases, but selectivity of the ether decomposition to IPA decreases. A maximum single pass yield of IPA from IPE of between about 50 weight % and about 60 weight % can be obtained by controlling the temperature, pressure, flow rate and water injection ratio. Alternatively, a lower single pass yield at a lower temperature could be desirable to increase the selectivity, but the amount of recycle ether is increased due to lower conversion at the lower temperature.

FIG. 5 shows that certain impurities, typically a mixture of $C_5, C_6, C_7$ and $C_{9+}$ compounds, from the ether decomposition of IPE increase as the ether decomposition temperature increases. However, even at the highest temperatures of about 280° C., the impurities were generally less than twice their values for the ether decomposition reaction at 230° C. FIG. 5 shows that the per pass weight % of impurities is about 1.5 weight % at a temperature of about 280° C. The data for FIG. 5 is listed in Table 7.

Based on the data in Table 7, a temperature of less than about 280° C. is desirable with respect to maintaining total impurities to less than or equal to about 1.5 weight %, preferably less than about 270° C. to maintain total impurities to less than or equal to about 1.1 weight %, preferably less than about 260° C. to maintain total impurities to less than or equal to about 0.7 weight %, preferably less than about 250° C. to maintain total impurities to less than or equal to about 0.7 weight %, preferably less than about 240° C. to maintain total impurities to less than or equal to about 0.7 weight %, and preferably less than about 230° C. to maintain total impurities to less than or equal to about 0.6 weight %.

TABLE 7

Pilot Plant Heavies versus Temperature

| Item | Average Bed Temp. °C. | Other C5s Wt. % | Other C6s Wt. % | Other C7s Wt. % | Other C9s+ Wt. % |
|---|---|---|---|---|---|
| 1 | 230 | 0.045 | 0.15 | | 0.00 |
| 2 | 230 | 0.006 | 0.17 | 0.03 | 0.40 |
| 3 | 240.0 | 0.011 | 0.27 | 0.15 | 0.45 |
| 4 | 239.9 | 0.012 | 0.26 | 0.13 | 0.43 |
| 5 | 240.0 | 0.009 | 0.19 | 0.09 | 0.35 |
| 6 | 239.9 | 0.006 | 0.22 | 0.05 | 0.37 |
| 7 | 239.9 | 0.006 | 0.22 | 0.03 | 0.37 |
| 8 | 239.9 | 0.009 | 0.20 | 0.04 | 0.36 |
| 9 | 247.6 | 0.010 | 0.25 | 0.27 | 0.41 |
| 10 | 247.6 | 0.001 | 0.24 | 0.27 | 0.39 |
| 11 | 247.7 | 0.001 | 0.24 | 0.26 | 0.40 |
| 12 | 247.1 | 0.008 | 0.24 | 0.07 | 0.40 |
| 13 | 265.6 | 0.042 | 0.45 | 0.11 | 0.93 |
| 14 | 247.2 | 0.010 | 0.24 | 0.02 | 0.42 |
| 15 | 262.2 | 0.005 | 0.24 | 0.03 | 0.43 |
| 16 | 262.1 | 0.010 | 0.23 | 0.02 | 0.38 |
| 17 | 247.2 | 0.008 | 0.23 | 0.13 | 0.35 |
| 19 | 255.0 | 0.010 | 0.25 | 0.28 | 0.38 |
| 20 | 254.9 | 0.017 | 0.27 | 0.06 | 0.45 |
| 21 | 255.3 | 0.023 | 0.34 | 0.09 | 0.58 |
| 22 | 254.9 | 0.019 | 0.33 | 0.09 | 0.54 |
| 23 | 254.9 | 0.012 | 0.27 | 0.06 | 0.46 |
| 24 | 254.8 | 0.012 | 0.26 | 0.03 | 0.46 |
| 25 | 270.1 | 0.035 | 0.43 | 0.07 | 0.75 |
| 26 | 269.9 | 0.008 | 0.37 | 0.05 | 0.37 |
| 27 | 270.0 | 0.026 | 0.38 | 0.05 | 0.63 |
| 28 | 270.1 | 0.027 | 0.41 | 0.07 | 0.65 |
| 29 | 280.0 | 0.034 | 0.49 | 0.19 | 0.78 |

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

We claim:

1. A process for the production of an alcohol, the process comprising:
    (a) reacting an olefin and water in the presence of a catalyst under conditions sufficient to form a crude alcohol stream comprising the alcohol and a dialkyl ether;
    (b) separating at least a portion of the crude alcohol stream into an alcohol-containing stream and a dialkyl ether stream;
    (c) contacting at least a portion of the dialkyl ether stream with an ether decomposition catalyst, the ether decomposition catalyst comprising:

a mixed metal oxide having the following composition:

where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising the alcohol and the olefin;

(d) recovering at least a portion of the olefin from the crude dialkyl ether decomposition stream; and (e) recycling at least a portion of the olefin recovered in step (d) to step (a).

2. The process according to claim 1, wherein the crude dialkyl ether decomposition stream comprises residual dialkyl ether, and the process further comprises the step of recycling at least a portion of the residual dialkyl ether to step (c).

3. The process according to claim 1, wherein at least a portion of the alcohol from the crude dialkyl ether decomposition stream is combined with the alcohol obtained at step (b).

4. The process according to claim 1, wherein the dialkyl ether has a formula $C_xH_{2x+1}OC_xH_{2x+1}$, wherein x ranges from about 2 to about 10.

5. The process according to claim 4, wherein x ranges from 2 to 4.

6. The process according to claim 1, wherein step (a) is a direct olefin hydration process or an indirect olefin hydration process.

7. The process according to claim 6, wherein the direct olefin hydration process operates at a pressure ranging from about 200 psig (1379 kPag) to about 2000 psig (13790 kPag), a temperature ranging from about 80° C. to about 120° C., a WHSV ranging from about 0.1 hr$^{-1}$ to about 5 hr$^{-1}$, a water to alcohol molar ratio ranging from about 0.1 to about 20, and the catalyst selected from acidic resins, solid phosphoric acid (SPA) catalysts, acidic zeolites, solid metal oxide catalysts, mixed metal oxides, and silicotungstate catalysts.

8. The process according to claim 6, wherein the indirect olefin hydration process operates at a pressure ranging from about 50 psig (345 kPag) to about 500 psig (3448 kPag), a temperature ranging from about 65° C. to about 120°C., a WHSV ranging from about 0.2 hr$^{-1}$ to about 0.8 hr$^{-1}$, a water to alcohol molar ratio ranging from about 1 to about 4, and the catalyst selected from sulfuric acid and phosphoric acid.

9. The process according to claim 1, wherein step (d) comprises a distillation.

10. The process according to claim 1, wherein step (c) operates at a pressure ranging from about 0 psig (0 kPag) to about 500 psig (3448 kPag).

11. The process according to claim 10, wherein step (c) operates at a pressure ranging from about 50 psig (345 kPag) to about 250 psig (1724 kPag).

12. The process according to claim 1, wherein step (c) operates at a pressure ranging from about 150 psig (1034 kPag) to about 210 psig (1448 kPag).

13. The process according to claim 1, wherein step (c) operates at a WHSV ranging from about 0.1 hr$^{-1}$ to 250 hr$^{-1}$.

14. The process according to claim 10, wherein step (c) operates at a WHSV ranging from about 1 hr$^{-1}$ to 100 hr$^{-1}$.

15. The process according to claim 1, wherein a molar ratio of water to dialkyl ether ranges from about 0.1 to about 5.0 in step (c).

16. The process according to claim 15, wherein the molar ratio of water to dialkyl ether ranges from about 0.5 to about 2.0.

17. The process according to claim 1, wherein an alcohol yield per pass ranges from about 10 weight % to about 90 weight %.

18. The process according to claim 17, wherein the alcohol yield per pass ranges from about 40 weight % to about 60 weight %.

19. The process according to claim 1, wherein the olefin recovered in step (d) has a purity of at least about 95 weight %.

20. The process according to claim 1, wherein the at least one metal selected from Group 3 and Group 6 of the Periodic Table of Elements comprises cerium, the at least one metal selected from Group 4 of the Periodic Table of Elements comprises zirconium, n is from about 0.02 to about 0.06, and p is from about 0 to about 0.05.

21. The process according to claim 1, wherein the mixed metal oxide further comprises sulfur, and has the composition $X_mY_nZ_pO_qS_r$ where X, Y, Z, m, n, p and q have the same meaning as in the preceding claims, and S is sulfur and r is the atomic ratio of sulfur.

22. The process according to claim 21, wherein the sulfur is present in an amount up to 5% by weight of the total mixed metal oxide composition, wherein Y is cerium, X is zirconium and p=0.

23. A process of improving the selectivity of olefin conversion in an olefin hydration process, the process comprising:

(a) contacting a dialkyl ether stream from the olefin hydration process with an ether decomposition catalyst, the ether decomposition catalyst comprising:

a mixed metal oxide having the following composition:

where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising an alcohol and an olefin;

(b) recovering at least a portion of the olefin from the crude dialkyl ether decomposition stream; and (c) using at least a portion of the olefin recovered in step (b) in the olefin hydration process used to make the dialkyl ether decomposed in step (a).

24. A process for the production of alcohols by dialkyl ether decomposition, the process comprising:

(a) reacting a mixture of olefins and water in the presence of a catalyst under conditions sufficient to form a first crude mixed alcohol stream comprising the water, a first mixture of alcohols, and a first mixture of dialkyl ethers;

(b) recovering at least a portion of the first mixture of dialkyl ethers;

(c) contacting at least a portion of the first mixture of dialkyl ethers recovered at step (b) with an ether decomposition catalyst, the ether decomposition catalyst comprising:

a mixed metal oxide having the following composition:

where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p, and q are the atomic ratios of their respective components and, when m is 1, n is from about 0.01 to about 0.75, p is from 0 to about 0.1, and q is the number of oxygen atoms necessary to satisfy the valence of the other components, to form a crude dialkyl ether decomposition stream comprising a second mixture of alcohols and a second mixture of olefins;

(d) recovering at least a portion of the second mixture of olefins from the first crude dialkyl ether decomposition stream; and (e) recycling at least a portion of the olefins recovered in step (d) to step (a).

25. A process for the production of an alcohol from an olefin and water, the process comprising:

(a) reacting the olefin and the water in the presence of a catalyst under conditions sufficient to form a first crude alcohol stream comprising the alcohol, the water and a dialkyl ether;

(b) separating the first crude alcohol stream into a water-alcohol mixture and a dialkyl ether stream;

(c) contacting at least a portion of the dialkyl ether stream with an ether decomposition catalyst to form a crude dialkyl ether decomposition stream comprising the alcohol, residual dialkyl ether, the olefin and the water, wherein a molar ratio of the water to the residual dialkyl ether is less than 3.0;

(d) recovering at least a portion of the olefin from the crude dialkyl ether decomposition stream;

(e) recycling at least a portion of the olefin recovered in step (d) to step (a);

(f) recovering at least a portion of the dialkyl ether from the crude dialkyl ether decomposition stream to form a second dialkyl ether stream and a second crude alcohol stream;

(g) recycling at least a portion of the second dialkyl ether stream to step (c); and (h) combining at least a portion of the second crude alcohol stream with the first crude alcohol stream.

* * * * *